(12) United States Patent
Mullins

(10) Patent No.: US 6,342,519 B2
(45) Date of Patent: Jan. 29, 2002

(54) OXETANONE DERIVATIVES

(75) Inventor: John Jason Gentry Mullins, San Francisco, CA (US)

(73) Assignee: 2 Pro Chemical, Dover, DE (US)

( * ) Notice: Subject to any disclaimer, the term of this patent is extended or adjusted under 35 U.S.C. 154(b) by 0 days.

(21) Appl. No.: 09/746,345

(22) Filed: Dec. 21, 2000

Related U.S. Application Data

(63) Continuation-in-part of application No. 09/698,307, filed on Oct. 27, 2000, which is a continuation-in-part of application No. 09/618,328, filed on Jul. 18, 2000, now abandoned, which is a continuation-in-part of application No. 09/431,551, filed on Oct. 29, 1999, now Pat. No. 6,235,305

(60) Provisional application No. 60/165,960, filed on Nov. 17, 1999.

(51) Int. Cl.$^7$ .................... A61K 31/337; C07D 305/12
(52) U.S. Cl. ...................... 514/449; 549/328; 424/1.73; 424/439
(58) Field of Search .................. 549/328; 514/449; 424/1.73, 439

(56) References Cited

U.S. PATENT DOCUMENTS 4,189,438 A * 2/1980 Umezawa et al.
5,643,874 A * 7/1997 Bremer et al.

FOREIGN PATENT DOCUMENTS

EP 444 482 A2 * 9/1991

\* cited by examiner

Primary Examiner—T. A. Solola
(74) Attorney, Agent, or Firm—Robert G. Lev

(57) ABSTRACT

This invention relates to novel oxetanone derivative compounds and processes for producing such derivatives that are useful as lipase inhibitors. Further the invention relates to processes for producing salts and for producing pharmaceutical compositions compounds comprising at least one such oxetanone derivative or salt, as well as methods for using such compounds and compositions for inhibiting lipases.

23 Claims, No Drawings

OXETANONE DERIVATIVES

The present application is a continuation-in-part of Ser. No. 09/698,307 Oct. 27, 2000, which is a continuation-in-part of Ser. No. 09/618,328, filed Jul. 18, 2000, abandoned which is a continuation-in-part of Ser. No. 09/431,551 filed Oct. 29, 1999, now U.S. Pat. No. 6,235,305 which is a continuation-in-part of Ser. No. 60/165,960, filed Nov. 17, 1999.

FIELD OF THE INVENTION

This invention relates to novel oxetanone derivative compounds and processes for producing such derivatives which are useful as lipase inhibitors. Further the invention relates to processes for producing salts and for producing pharmaceutical compositions compounds comprising at least one such oxetanone derivative or salt, as well as methods for using such compounds and compositions for inhibiting lipases. In one aspect the invention relates to lipase inhibitors which include on the same molecule an oxetanone derivative portion capable of inhibiting a lipase and a non-absorbable moiety such a polysaccharide, which are covalently linked or are in the form of a salt. In a preferred aspect of the invention the non-absorbable moiety is lipophilic and will associate with oils or fats. An absorbable oxetanone lipase inhibitor may be rendered non-absorbable by covalent linking it directly or indirectly to a non-absorbable moiety and thereby producing a novel non-absorbable lipase inhibitor.

BACKGROUND OF THE INVENTION

Some lipase-inhibiting oxetanones and intermediates for making them are well known. See for example, U.S. Pat. Nos. 5,931,463, 4,189,438 and 4,202,824. However, there is a need for improved oxetanones that are have low toxicity and are essentially not absorbable by the digestive system of mammals such as dogs, cats, non-human primates and human primates.

Lipase inhibitors such as esterastin (see U.S. Pat. No. 4,189,438), tetrahydroesterastin (3,5-hydroxy-2hexadeca-7, 10-dienoic 1,3-lactone), 3,5-dihydroxy-2-hexylhexadeca-7, 10-dienoic 1,3-lactone, 3,5-di-hydroxy-2-hexylhexadecanoic 1,3-lactone, and the like, are well-known as lipase inhibitors and as pancreatic cholesterol esterase inhibitors. However, such lipase inhibitors are, inter alia, also substantially orally active as immunosuppressants (see U.S. Pat. No. 4,189,438 and U.S. Pat. No. 4,202,824), which can be a highly undesired side activity in a normal or immunosuppressed person. Such lipase inhibitor compounds are 3,5 dihydroxy 1,3 lactone derivative compounds, wherein the 5-hydroxyl group may be esterified at the 5 position or is hydrolyzed to the free hydroxyl group.

A popular lipase inhibiting compound which is substantially non-absorbable is known as Orlistat ((2S,3S,5S)-5-[(S)-2-formamido-4-methyl-valeryloxy]-2-hexyl-3-hydroxy-hexadecanoic 1,3 acid lactone, see U.S. Pat. No. 5,643,874). This compound is a steric isomer derivative of tetrahydroesteratin and its 5-hydroxyl group is esterified with a [S-2-formamido-4-methyl-valeryloxy] group. Orlistat has been used to inhibit lipases in the body and thereby prevent the absorption of dietary fat. At a 120 mg dose of Orlistat, taken before consuming a fat-containing meal (or up to one hour after eating such a meal), up to one-third of the fat eaten at a given meal will not be absorbed by the average person and utilized as dietary fat calories. The undigested fat passes directly through the digestive system as an oil and is eliminated from the bowel in its oily undigested form.

Certain polysaccharides are non-absorbable and some polysaccharides have the side benefit of reducing lipid absorption by the body. Defatted rice germ polysaccharides and sulfated polysaccharides are also lipase inhibitors, which are high molecular weight compounds that do not appear to have any lactone moieties and seem to work by a different mechanism, binding the lipase and removing it from the digestive system when they are discharged from the digestive system. The super fiber Chitosan, which is a deacylated polysaccharide derived from shellfish chitan, has an ability to absorb fat and cholesterol, particularly in combination with vitamin C. Chitosan compositions may actually absorb up to 6 to 8 times their weight in fat and oils. While the polysaccharide from shellfish is similar to crude cellulose plant fiber, it has the ability to significantly bind fat in the digestive system as compared to plant fiber. Further, since polysaccharides, including those which do not preferentially bind oils over water, are not absorbed by the digestive systems of animals such as humans, non-human primates, dogs and cats, there is no caloric value to such polysaccharides and they pass through the such digestive systems unabsorbed and substantially intact. Examples of non-absorbable polysaccharides are polysaccharides having a molecular weight of greater than 8 kDa such as dextrans, molecular microcrystalline cellulose, wheat bran, oat bran, defatted rice germ, alginic acid, pectin, amylopectin, chitin, crude cellulose, argar, chitosan and the like.

There is a need in the art for non-absorbable lipase inhibitors, as well as for improved antiadiposity compositions and methods which do not require an absolute low-fat diet in order to lower the absorption of dietary fat as calories.

SUMMARY OF THE INVENTION

In one aspect the present invention relates to novel derivatives of lipase inhibitors which are non-absorbable compounds comprising at least one lipase inhibitor moiety and at least one non-absorbable polymeric moiety in the same molecule or salt. The lipase inhibitor moiety is preferably present in the non-absorbable compound in a weight ratio of from about 1:10 to about 1:60 with respect to the weight of the polymeric moiety, preferably from about 1:20 to about 1:40, and more preferably from about 1:25 to 1:35. In one aspect, such lipase inhibitors comprise at least one lipase inhibitor moiety (or moieties) linked directly or indirectly to such a polymeric moiety. The invention also includes pharmaceutical compositions comprising an effective amount of such lipase inhibitors in combination with a pharmaceutically acceptable carrier or diluent, which compositions may further comprise an effective amount of a lipophilic, non-absorbable biocompatible, pharmaceutically acceptable oil absorbing polymer.

In another aspect the present invention relates to novel salts of non-absorbable lipase inhibitors and a non-absorbable biocompatible, pharmaceutically acceptable oil absorbing polymer. The invention also includes pharmaceutical compositions comprising an effective amount of such lipase inhibitors in combination with a pharmaceutically acceptable carrier or diluent, which compositions may further comprise an effective amount of a lipophilic, non-absorbable biocompatible, pharmaceutically acceptable oil absorbing polymer.

In a preferred aspect the present invention relates to novel non-absorbable derivatives of a 1,3 oxetanone lipase inhibitor, which include at least one 1,3 oxetanone lipase inhibiting moiety that is covalently or non-covalently linked to a non-absorbable biocompatible, pharmaceutically acceptable polymer moiety to provide a novel lipase inhibitor compound. Preferred compounds have the dual function of inhibiting lipases and absorbing fat, in that the non-absorbable biocompatible, pharmaceutically acceptable polymer moiety of the novel lipase inhibitor will bind to fat, carry the bound fat with it through portions of the digestive system and cause the non-absorbed fat to be eliminated removed from the digestive system as undigested fat. The 1,3 oxetanone moiety that is derivatized directly or indirectly with the polymer moiety according to the invention may be initially an absorbable or non-absorbable moiety and is derivatized by directly or indirectly linking it to the polymer moiety to form a novel non-absorbable lipase inhibitor, preferably at the 5 hydroxyl position of a 1,3 oxetanone moiety.

In a preferred aspect the invention provides compounds having either non-covalent linkages of such two moieties or covalent linkages that are hydrolyzed or digested in the digestive system, providing that the lipase inhibiting 1,3 oxetanone derivative moiety that is released in the digestive system is substantially non-absorbable.

In another preferred aspect the invention provides compounds having either a non-covalent linkage of such two moieties or a covalent linkage that is not hydrolyzed or digested in the digestive system, whereby the lipase inhibiting 1,3 oxetanone derivative moiety remains linked to the polymer moiety via such non-covalent or covalent linkage and is not released in the digestive system.

In one aspect of the invention, an absorbable lipases such as esterastin moiety, tetrahydroestrastin, or a similar moiety, is rendered non-absorbable by coupling it directly or indirectly to a non-absorbable biocompatible, pharmaceutically acceptable polymer moiety, such as a polysaccharide, to render the lipase essentially non-absorbable by the digestive system of an animal such as a dog, cat, non-human primate or humans. Preferred lipase inhibitor moieties that are coupled to the polysaccharide include at least one lipase inhibitor which is a member selected from the group consisting of esterastin, tetrahydro-esterastin (3,5-hydroxy-2-hexadeca-7, 10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like. Preferably, such lipase inhibitor is coupled to a non-absorbable biocompatible, pharmaceutically acceptable polymer moiety, such as a polysaccharide, to render the lipase non-absorbable by the digestive system of an animal such as a dog, cat, non-human primate or humans. Particularly preferred polysaccharides have at least one member selected from the group consisting of dextrans, molecular microcrystalline cellulose, wheat bran, oat bran, defatted rice germ, alginic acid, pectin, amylopectin, chitin, crude cellulose, argar, chitosan, a chitosan methylbenzoic acid ester ether derivative, and the like. Particularly preferred bound lipase inhibitors are lipase inhibitors bound via a derivatized group on the lipase such as a derivatized nitrogen, acid or alcohol group to a group on the polymer moiety such as a derivatized alcohol, acid or amino group. Preferably, a divalent bridging group is attached at one portion of the bridging group to an amino group on the polysaccharide and attached at a second portion of the bridging group to a lipase inhibitor and the moiety. Further preferred are such compounds wherein further amino groups, alcohol groups or amino groups and alcohol groups on the polysaccharide are modified to present open organic acyl group sufficient to render the polysaccharide capable of associating with both organic neutral to acid groups and polar inorganic groups such as water such that a homogeneous gel can be formed. Also preferred are compounds wherein the lipase inhibitor is an oxetanone moiety which is derivatized to provide an amino group which is further derivatized to form a carboxamide group, followed by linking the carboxamide group to an acid group, alcohol group or amino group on the polymer moiety via a bridging group, which polymer moiety may have been derivativized in order to provide such an acid or alcohol group for attachment. Examples of such attachments are illustrated below by a preferred embodiment of the invention.

In another aspect the present invention relates to pharmaceutical compositions comprising a lipase inhibiting effective amount of at least one lipase inhibitor which is coupled to a digestively non-absorbable moiety. Preferred are such pharmaceutical compositions comprising an effective amount of a lipases coupled to a non-absorbable biocompatible, pharmaceutically acceptable polymer moiety, such as a polysaccharide, wherein the lipase is essentially non-absorbable by the digestive system of an animal such as a dog, cat, non-human primate or humans.

In still another aspect, the present invention relates to a method for treating adiposity or obesity by administering to a patient before a fat-contain meal, or up to one hour after such a meal is consumed, an amount of at least one lipase inhibitor which is bound to a non-absorbable polymer moiety in an amount effective to inhibit the absorption of up to one-third of the dietary fat in such a meal. In particular, a preferred method comprises administering at one lipase inhibitor which is a member selected from the group consisting of esterastin, tetrahydro-esterastin (3,5-hydroxy-2hexadeca-7,10-dienoic 1,3-lactone), 3,5-dihydroxy-2-hexylhexadeca-7, 10-dienoic 1,3-lactone, 3,5-di-hydroxy-2-hexylhexadecanoic 1,3-lactone, and the like, wherein such lipase inhibitor is coupled to a non-absorbable biocompatible, pharmaceutically acceptable polymer moiety, such as a polysaccharide, to render the lipase non-absorbable by the digestive system of an animal such as a dog, cat, non-human primate or humans. Particularly preferred polysaccharides are at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred bound lipase inhibitors are lipase inhibitors bound via a derivatized nitrogen, acid or alcohol group to a derivatized alcohol, acid or amino group on the polymer moiety.

A divalent bridge terminal amino attachment/terminal ester bridge, between the lipase inhibitor moiety and the polymer moiety which is derived from an alcohol group on the lipase inhibitor moiety and an amino group on the polymer moiety, respectively reacting with a bridging group is a preferred coupling of the lipase inhibitor to the moiety.

Another preferred bridge between the lipase inhibitor moiety and the polymer moiety includes at least amino terminal bridge formed from an amino group on the polymer moiety and at least one carboxamide bond terminal bridge attachment to the lipase inhibitor derivative. Further preferred are compounds wherein at least one amino acid derivative is located in the bridge, and is bound directly or indirectly to the 5 hydroxyl position on the 1,3 oxetanone lipase inhibitor moiety via an ester linkage.

The preferred compounds also include their pharmaceutically acceptable isomers, hydrates, solvates, salts and pro-drug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

The term "bridging group" refers to a bifunctional chain or spacer group capable of reacting with one or more functional groups on a lipase inhibitor compound and then react with a second same or different functional group on a polymer compound in order to form a linked structure or conjugate between the two compounds. The bond formed between the bridging group and each of the two moieties is preferably of a type that is resistant to cleavage by the digestive environment when the linked lipase moiety would be absorbable upon cleavage of the bond. In one aspect, the bridging group is of the formula X-R-X, wherein R is a member selected from a straight-chained or branched alkyl group, a straight-chained or branched alkenyl group, a straight-chained or branched alkynyl group, a mono acyl group, a diacyl group and the like, which R portion of the chain may include a cycloalkyl or an aryl group, and X is a functionally reactive group such as a halogen, or acid group, under special reaction conditions as described hereinafter. Particularly preferred bridging groups form a ester terminal and amino terminal, ether terminal/acyl terminal bridge that is resistant to cleavage by the digestive environment. In one aspect bridging groups that are cleaved by the digestive group to release an essentially non-absorbable lipase inhibitor are preferred. Examples of alkylene halogen terminal/acyl terminal bridging group forming compounds are a $C_2$ to $C_{20}$ n-haloalkanoic acid or an ester thereof, such as 6-bromohexanoic acid, 12-bromolauric acid, haloloweralkylbenzoic acid, and the like.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to $—CH_2—$.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In one aspect the present invention relates to novel derivatives of lipase inhibitors which are non-absorbable and have a lipase inhibitor moiety and polymeric moiety in the same molecule. The invention also includes pharmaceutical compositions comprising an effective amount of such lipase inhibitors in combination with a pharmaceutically acceptable carrier or diluent, and may further comprise an effective amount of a lipophilic, non-absorbable biocompatible, pharmaceutically acceptable oil absorbing polymer. The lipase inhibitor moiety is present in a weight ratio of from about 1:10 to about 1:60 with respect to the weight of the polymeric moiety, preferably from about 1:20 to about 1:40, and more preferably from about 1:25 to 1:35. In one aspect, such lipase inhibitors comprise at least one lipase inhibitor moiety (or moieties) linked directly or indirectly to such polymeric moiety.

In another aspect the present invention relates to novel salts of non-absorbable lipase inhibitors and a non-absorbable biocompatible, pharmaceutically acceptable oil absorbing polymer. The invention also includes pharmaceutical compositions comprising an effective amount of such lipase inhibitors in combination with a pharmaceutically acceptable carrier or diluent, which compositions may further comprise an effective amount of a lipophilic, non-absorbable biocompatible, pharmaceutically acceptable oil absorbing polymer.

In a preferred aspect the present invention relates to novel essentially non-absorbable derivatives of a 1,3 oxetanone lipase inhibitor, which include at least one 1,3 oxetanone lipase inhibiting moiety that is covalently or non-covalently linked to a non-absorbable biocompatible, pharmaceutically acceptable polymer moiety to provide a novel lipase inhibitor compound. Preferred compounds have the dual function of inhibiting lipases and absorbing fat, in that the non-absorbable biocompatible, pharmaceutically acceptable polymer moiety of the novel lipase inhibitor will bind to fat, carry the bound fat with it through portions of the digestive system and cause the non-absorbed fat to be eliminated removed from the digestive system as undigested fat. Further preferred are such compounds wherein the compound is capable of associating with both oil and water to form an essentially homogeneous gel. The 1,3 oxetanone moiety that is derivatized directly or indirectly with the polymer moiety according to the invention may be initially an absorbable or non-absorbable moiety and is derivatized by directly or indirectly linking it to the polymer moiety to form a novel non-absorbable lipase inhibitor, preferably at the 5 hydroxyl position of a 1,3 oxetanone moiety.

In a preferred aspect the invention provides compounds having either non-covalent linkages of such two moieties or covalent linkages that are hydrolyzed or digested in the digestive system, providing that the lipase inhibiting 1,3 oxetanone derivative moiety that is released in the digestive system is substantially non-absorbable.

In one aspect of the invention, lipases such as esterastin moiety, tetrahydroestrastin, or a similar moiety, is coupled directly or indirectly to a non-absorbable biocompatible, pharmaceutically acceptable polymer moiety, such as a polysaccharide, to render the lipase essentially non-absorbable by the digestive system of an animal such as a dog, cat, non-human primate or humans. Preferred absorbable lipase inhibitor moieties that are rendered non-absorbable by such coupling include at least one lipase inhibitor which is a member selected from the group consisting of esterastin, tetrahydro-esterastin (3,5-hydroxy-2-hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like. Preferably, such lipase inhibitor is coupled to a non-absorbable biocompatible, pharmaceutically acceptable polymer moiety, such as a polysaccharide, to render the lipase non-absorbable by the digestive system of an animal such as a dog, cat, non-human primate or humans. Particularly preferred polysaccharides have at least one member selected from the group consisting of dextrans, molecular microcrystalline cellulose, wheat bran, oat bran, defatted rice germ, alginic acid, pectin, amylopectin, chitin, crude cellulose, argar, chitosan, a chitosan methylbenzoic acid ester ether derivative, and the like. Particularly preferred bound lipase inhibitors are lipase inhibitors bound via a derivatized group on the lipase such as a derivatized nitrogen, acid or alcohol group to a group on the polymer moiety such as a derivatized alcohol, acid or amino group. Preferably, amino groups, alcohol groups or both amino and alcohol groups on the polysaccharide has been derivitized with a sufficient number of organic acyl groups to render the polysaccharide capable of associating with both oil and water and thereby form an essentially homogeneous gel. Preferably, a terminal ether/terminal acyl ester bridge or a terminal amino/terminal acyl ester bridge is formed between the lipase inhibitor and the moiety, wherein the bridge is derived from an alcohol group on the lipase and an alcohol or amino group on the polysaccharide moiety, each reacting the polysaccharide with an etherizing or amino forming bridging group to present an acyl group, which may be a free acyl group or ester group. Also preferred are compounds wherein the oxetanone moiety of lipase inhibitor is derivatized to provide an amino group which is further derivatized to form a carboxamide group, followed by linking the carboxamide group to an acid, amino or alcohol group on the polymer moiety via a bridging group, which polymer moiety may have been derivativized in order to provide such an acid, alcohol or amino group for attachment. Examples of such attachments are illustrated below by preferred embodiments of the invention.

An ether terminal/ester terminal or amino terminal/ester terminal, between the lipase inhibitor moiety and the polymer moiety which is derived from an alcohol group on the lipase inhibitor moiety and an alcohol or amino group on the polysaccharidemoiety, respectively reacting with a bridging group is a preferred coupling of the lipase inhibitor to the moiety.

Another preferred bridge between the lipase inhibitor moiety and the polymer moiety includes at least one ether bridge or amino bridge formed from an alcohol group or amino group, respectively, on the polymer moiety and at least one carboxamide bond. Further preferred are compound wherein at least one amino acid derivative is located in the bridge, and is bound directly or indirectly to the 5 hydroxyl position on the 1,3 oxetanone lipase inhibitor moiety via an ester linkage.

The preferred compounds also include their pharmaceutically acceptable isomers, hydrates, solvates, salts and pro-drug derivatives.

A preferred aspect of the present invention relates to novel oxetanone derivatives of the formula I, as follows:

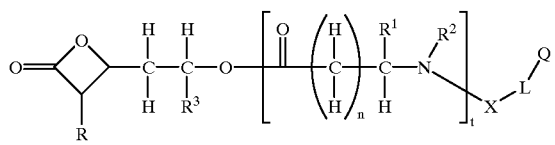

wherein:
t is an integer from 0 to 1
X-L-Q is an ether or amino linkage wherein:
X of the ether or amino linkage is a bridging group,
L is —O— or —NH—, and Q of the ether or amino linkage is a polysaccharide of a sufficient molecular weight or property that such polysaccharide is not absorbed by the digestive system of a mammal such as a dog, cat, non-human primate or a human primate, particularly preferred is wherein the hydroxyl groups, amino groups or hydroxyl and amino groups of Q are modified by the attachment of a sufficient number of organic acyl groups to cause Q to absorb or associate with both lipids and water and to form a substantially homogeneous gel with lipids and water;

R is a member selected from the group consisting of:
  a straight or branched chained $C_{1-17}$-alkyl group which is saturated or optionally interrupted by up to eight double or triple bonds;
  a straight or branched chained $C_{1-17}$-alkyl group which is saturated or optionally interrupted by one or more members selected from the group consisting of an oxygen atom, a sulfur atom, a sulfonyl group or a sulfinyl group;
  a straight or branched chained $C_{1-17}$-alkyl group which is saturated or optionally interrupted by up to eight double or triple bonds and is interrupted in a position other than alpha to an unsaturated carbon atom by one or more members selected from the group consisting of an oxygen atom, a sulfur atom, a sulfonyl group or a sulfinyl group atoms;
  phenyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  benzyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  phenylthiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and
  phenyl-$C_{1-6}$-alkyl-phenyl wherein 0-6 hydrogen atoms on one or more of the phenyl ring and —$C_{1-6}$-alkyl-group is/are replaced independently by a member selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

$R^1$ is a member selected from the group consisting of:
  Hydrogen,
  Ar,
  Ar—$C_{1-5}$-alkyl and
  $C_{1-10}$-alkyl interrupted by 0-3 members independently selected from the group consisting of an oxygen atom, a sulfur atom, a sulfinyl group, a sulfonyl group, a-N(—$R^4$)— group, a —C(=O)—N(—$R^4$)— group, and a —N(—$R^4$)—C(=O)— group, wherein 0-3 carbon atoms of the $C_{1-10}$-alkyl group can be substituted independently by a member selected from the group consisting of a hydroxy group, thiol group, $C_{1-10}$-alkoxy group, a $C_{1-10}$-alkylthio group, a —N(—$R^5$,—$R^6$) group, a —C(=O)—N(—$R^7$, —$R^8$) group, and a —N(—$R^9$)—C(=O)—$R^{10}$ group;

$R^2$ is a member selected from the group consisting of:
  hydrogen and $C_{1-6}$-alkyl, or $R^2$ taken with $R^1$ forms a 4-6 membered saturated ring containing 0-4 nitrogen atoms wherein the ring may be substituted by 0-4 $R^{11}$ groups;

$R^3$ is a member selected from the group consisting of:
  a straight or branched chained $C_{1-17}$-alkyl group which is saturated or optionally interrupted by up to eight double or triple bonds;
  a straight or branched chained $C_{1-17}$-alkyl group which is saturated or optionally interrupted by one or more members selected from the group consisting of an oxygen atom, a sulfur atom, a sulfonyl group or a sulfinyl group;
  a straight or branched chained $C_{1-17}$-alkyl group which is saturated or optionally interrupted by up to eight double or triple bonds and is interrupted in a position other than alpha to an unsaturated carbon atom by one or more members selected from the group consisting of an oxygen atom, a sulfur atom, a sulfonyl group or a sulfinyl group atoms;
  phenyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  benzyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  phenylthiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and
  phenyl-$C_{1-6}$-alkyl-phenyl wherein 0-6 hydrogen atoms on one or more of the phenyl ring and —$C_{1-6}$-alkyl-group is/are replaced independently by a member selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

$R^4$-$R^{10}$ are each independently a member selected from the group consisting of:
  hydrogen and $C_{1-6}$-alkyl;

n is an integer of 0-3;

and all pharmaceutically acceptable isomers, salts, hydrates, solvates and prodrug derivatives thereof.

Another preferred aspect of the present invention relates to novel oxetanone derivatives of the formula Ia, as follows:

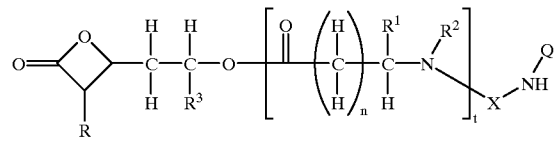

wherein:
  t is an integer from 0 to 1
  X—N(—H)-Q is an amino linkage of X to Q wherein:
    X of the amino linkage is a bridging group, and
    Q of the amino linkage is a polysaccharide of a sufficient molecular weight or property that such polysaccharide is not absorbed by the digestive system of a mammal such as a dog, cat, non-human primate or a human primate, particularly preferred is wherein the hydroxyl groups, amino groups or hydroxyl and amino groups of Q are modified by the attachment of a sufficient number of organic acyl groups to cause Q to absorb or associate with both lipids and water and to form a substantially homogeneous gel with lipids and water;
  R is a member selected from the group consisting of:
    a straight or branched chained $C_{1-17}$-alkyl group which is saturated or optionally interrupted by up to eight double or triple bonds;
    a straight or branched chained $C_{1-17}$-alkyl group which is saturated or optionally interrupted by one or more members selected from the group consisting of an oxygen atom, a sulfur atom, a sulfonyl group or a sulfinyl group;
    a straight or branched chained $C_{1-17}$-alkyl group which is saturated or optionally interrupted by up to eight double or triple bonds and is interrupted in a position other than alpha to an unsaturated carbon atom by one or more members selected from the group consisting of an oxygen atom, a sulfur atom, a sulfonyl group or a sulfinyl group atoms;
    phenyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    benzyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    phenyithiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and
    phenyl-$C_{1-6}$-alkyl-phenyl wherein 0-6 hydrogen atoms on one or more of the phenyl ring and —$C_{1-6}$-alkyl- group is/are replaced independently by a member selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
  $R^1$ is a member selected from the group consisting of:
    Hydrogen,
    Ar,
    Ar—$C_{1-5}$-alkyl and
    $C_{1-10}$-alkyl interrupted by 0-3 members independently selected from the group consisting of an oxygen atom, a sulfur atom, a sulfinyl group, a sulfonyl group, a-N(—$R^4$)— group, a —C(=O)—N(—$R^4$)— group, and a —N(—$R^4$)—C(=O)— group, wherein 0-3 carbon atoms of the $C_{1-10}$-alkyl group can be substituted independently by a member selected from the group consisting of a hydroxy group, thiol group, $C_{1-10}$-alkoxy group, a $C_{1-10}$-alkylthio group, a —N(—$R^5$,—$R^6$) group, a —C(=O)—N(—$R^7$, —$R^8$) group, and a —N(—$R^9$)—C(=O)—$R^{10}$ group;
  $R^2$ is a member selected from the group consisting of:
    hydrogen and $C_{1-6}$-alkyl, or $R^2$ taken with $R^1$ forms a 4-6 membered saturated ring containing 0-4 nitrogen atoms wherein the ring may be substituted by 0-4 $R^{11}$ groups;
  $R^3$ is a member selected from the group consisting of:
    a straight or branched chained $C_{1-17}$-alkyl group which is saturated or optionally interrupted by up to eight double or triple bonds;
    a straight or branched chained $C_{1-17}$-alkyl group which is saturated or optionally interrupted by one or more members selected from the group consisting of an oxygen atom, a sulfur atom, a sulfonyl group or a sulfinyl group;
    a straight or branched chained $C_{1-17}$-alkyl group which is saturated or optionally interrupted by up to eight double or triple bonds and is interrupted in a position other than alpha to an unsaturated carbon atom by one or more members selected from the group consisting of an oxygen atom, a sulfur atom, a sulfonyl group or a sulfinyl group atoms;
    phenyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    benzyl substituted by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
    phenylthiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and
    phenyl-$C_{1-6}$-alkyl-phenyl wherein 0-6 hydrogen atoms on one or more of the phenyl ring and —$C_{1-6}$-alkyl-group is/are replaced independently by a member selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and -$C_{1-6}$-alkyl-SH;
  $R^4$-$R^{10}$ are each independently a member selected from the group consisting of:
    hydrogen and $C_{1-6}$-alkyl;
  n is an integer of 0-3;
  and all pharmaceutically acceptable isomers, salts, hydrates, solvates and prodrug derivatives thereof.

A preferred compound according to formula I, or formula Ia, is a compound wherein X is a member selected from the group consisting of:

$$—(C(=O))_{0-1}—X_a—,$$

wherein $X_a$ is a member selected from the group consisting of:
- a straight or branched chained divalent $C_{1-17}$-alkylene group which is saturated or optionally interrupted by up to eight double or triple bonds;
- a straight or branched chained divalent $C_{1-17}$-alkylene group which is saturated or optionally interrupted by one or more members selected from the group consisting of:
  - an oxygen atom,
  - a sulfur atom,
  - a sulfonyl group,
  - a sulfinyl group,
  - a substituted or unsubstituted 6-10 member monocyclic or bicyclic aryl or heteroaryl group having from 1-4 ring hetero atoms selected from the group consisting of O, N, S,
  - a —NH— group, wherein the hydrogen atom may be replaced with a $C_{1-10}$ alkyl group
  - a —C(=O)— group,
  - a —NH—C(=O)— group, wherein the hydrogen atom may be replaced with a $C_{1-10}$ alkyl group and
  - a —C(=O)—NH— group, wherein the hydrogen atom may be replaced with a $C_{1-10}$ alkyl group
- a straight or branched chained divalent $C_{1-17}$-alkylene group which is saturated or optionally interrupted by up to eight double or triple bonds and is interrupted in a position other than alpha to an unsaturated carbon atom by one or more members selected from the group consisting optionally interrupted by one or more members selected from the group consisting of:
  - an oxygen atom,
  - a sulfur atom,
  - a sulfonyl group,
  - a sulfinyl group,
  - a substituted or unsubstituted 6-10 member monocyclic or bicyclic aryl or heteroaryl group having from 1-4 ring hetero atoms selected from the group consisting of O, N, S,
  - a —NH— group, wherein the hydrogen atom may be replaced with a $C_{1-10}$ alkyl group
  - a —C(=O)— group,
  - a —NH—C(=O)— group, wherein the hydrogen atom may be replaced with a $C_{1-10}$ alkyl group and
  - a —C(=O)—NH— group, wherein the hydrogen atom may be replaced with a $C_{1-10}$ alkyl group
- divalent phenylene or divalent naphthylene substituted on the ring structure by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
- divalent biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
- phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;
- divalent phenylthiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and
- and all pharmaceutically acceptable isomers, salts, hydrates, solvates and prodrug derivatives thereof.

Preferred sub-groups of such compounds are compounds wherein R is —$(CH_2)_{3-6}$—$CH_3$ and $R^3$ is a member selected from the group consisting of —$(CH_2)_{8-14}$—$CH_3$ and —$CH_2$—$CH$=$CH$—$CH_2$—$CH$=$CH$—$(CH_2)_{2-8}$—$CH_3$.

Even more preferred are such compounds wherein R is —$(CH_2)_5$—$CH_3$ and $R^3$ is a member selected from the group consisting of —$(CH_2)_{10}$—$CH_3$ and —$CH_2$—$CH$=$CH$—$CH_2$—$CH$=$CH$—$(CH_2)_4$—$CH_3$.

In a preferred embodiment, the present invention relates to novel oxetanone derivatives wherein n of the above formula is zero to provide compounds of the formula:

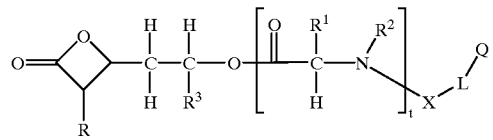

wherein:
X, L, t, Q, R, $R^1$, $R^2$ and $R^3$ are defined as above, and isomers, salts, hydrates, solvates and prodrug derivatives thereof. Preferred sub-groups of such compounds are compounds wherein R is —$(CH_2)_{3-6}$—$CH_3$ and $R^3$ is a member selected from the group consisting of —$(CH_2)_{8-14}$—$CH_3$ and —$CH_2$—$CH$=$CH$—$CH_2$—$CH$=$CH$—$(CH_2)_{2-8}$—$CH_3$. More preferred are such compounds wherein R is —$(CH_2)_5$—$CH_3$ and $R^3$ is a member selected from the group consisting of —$(CH_2)_{10}$—$CH_3$ and —$CH_2$—$CH$=$CH$—$CH_2$—$CH$=$CH$—$(CH_2)_4$—$CH_3$. Further preferred are compounds wherein t is 0 and X is —C(=O)—$X_a$— as set forth above.

Even further preferred are such compounds wherein t is 1 and X is a member selected from the group consisting of:

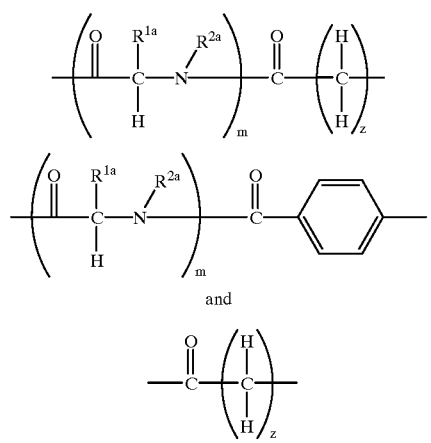

and wherein $R^{1a}$ is independently defined the same as defined for $R^1$, $R^{2a}$ is independently defined the same as for $R^2$, m is a integer from 0 to 10, preferably from 0-5, and more preferred from 0-2, and wherein z is an integer from 1 to 20, preferably 2 to 10, and more preferably, 2-4, and all pharmaceutically acceptable isomers, salts, hydrates, solvates and prodrug derivatives thereof.

In another preferred embodiment, the present invention relates to such novel oxetanone derivatives of formula 1 having the following formula:

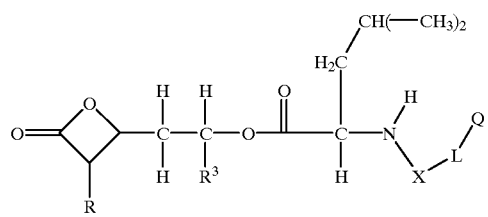

wherein:

X, L, Q, R, and $R^3$ are defined as above, and isomers, salts, hydrates, solvates and prodrug derivatives thereof. Preferred sub-groups of such compounds are compounds wherein R is —$(CH_2)_{3-6}$—$CH_3$ and $R^3$ is a member selected from the group consisting of —$(CH_2)_{8-14}$—$CH_3$ and —$CH_2$—$CH$=$CH$—$CH_2$—$CH$=$CH$—$(CH_2)_{2-8}$—$CH_3$. More preferred are such compounds wherein R is —$(CH_2)_5$—$CH_3$ and $R^3$ is a member selected from the group consisting of —$(CH_2)_{10}$—$CH_3$ and —$CH_2$—$CH$=$CH$—$CH_2$—$CH$=$CH$—$(CH_2)_4$—$CH_3$.

Even further preferred are such compounds wherein X is a member selected from the group consisting of:

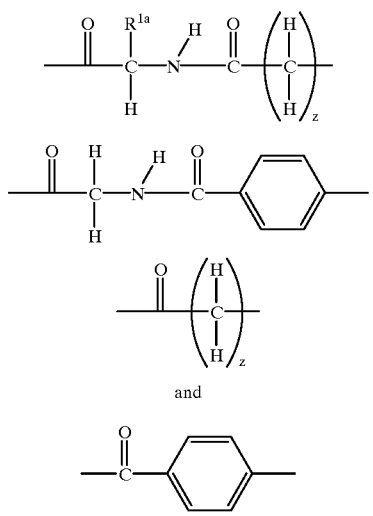

wherein z is a integer from 0 to 10, preferably from 0-5, and more preferred from 0-2.

and all pharmaceutically acceptable isomers, salts, hydrates, solvates and prodrug derivatives thereof.

Other preferred compounds are compounds, wherein t is 0 or 1 and X is a member selected from the group consisting of:

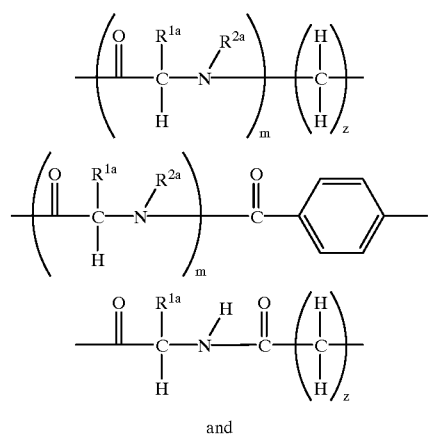

and

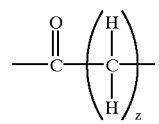

wherein $R^{1a}$ is independently defined the same as defined for $R^1$, $R^{2a}$ is independently defined the same as for $R^2$, m is a integer from 0 to 10, preferably from 0–5, and more preferred from 0–2, and wherein z is an integer from 1 to 20, preferably 2 to 10, and more preferably, 2–4, and all pharmaceutically acceptable isomers, salts, hydrates, solvates and prodrug derivatives thereof. One preferred group of compounds are such compounds wherein L is —NH— and another preferred group of compounds are such compounds wherein L is —O—.

The above compound, wherein X is a member selected from the group consisting of:

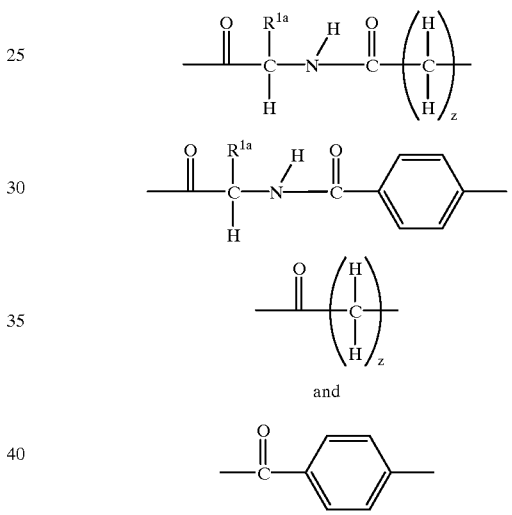

and wherein z is a integer from 0 to 10, preferably from 0-5, and more preferred from 0-2, and all pharmaceutically acceptable isomers, salts, hydrates, solvates and prodrug derivatives thereof.

Further preferred are such compounds, wherein X is a member selected from the group consisting of:

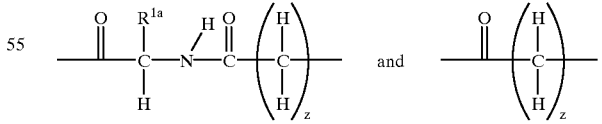

and wherein z is a integer from 0 to 18, and all pharmaceutically acceptable isomers, salts, hydrates, solvates and prodrug derivatives thereof. One preferred group of such compounds is wherein L is —NH— and another preferred group of such compound is wherein L is —O—.

Additionally preferred are such compounds wherein X is a member selected from the group consisting of:

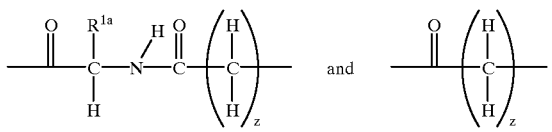

and wherein z is a integer 6–12,
and all pharmaceutically acceptable isomers, salts, hydrates, solvates and prodrug derivatives thereof. One preferred group of such compounds is wherein L is —NH— and another preferred group of such compound is wherein L is —O—.

More preferred are such compounds wherein X is a member selected from the group consisting of:

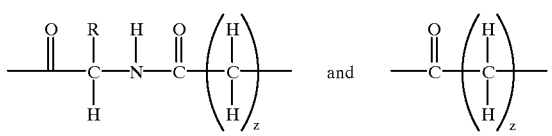

and wherein z is a integer 6–12,
and all pharmaceutically acceptable isomers, salts, hydrates, solvates and prodrug derivatives thereof. One preferred group of such compounds is wherein L is —NH— and another preferred group of such compound is wherein L is —O—.

Particularly preferred Q groups for the above compounds are non-absorbable biocompatable, pharmaceutically acceptable polymers, such as a polysaccharide, which are preferably lipophilic and bind to fat and are non-absorbable by the digestive system of an animal such as a dog, cat, non-human primate or humans. Particularly preferred polysaccharides have at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred Q groups have an alcohol, acyl group or amino group, or can be derivatized to present such an alcohol, acyl or amino group, which can be bound to the R moiety or the X—R—X group Preferably, at least one and or two ether bridges can be formed between a lipase inhibitor moiety and the polymer moiety via an X—R—X bridge, wherein the bridge is derived from an alcohol group or amine group on the lipase and an alcohol group, acyl group or amino group on the Q group. Even more preferred are Q groups which are chitosan derivatives that have been modified by an ether group or amino group which is terminated by an organic acid group. Further preferred are such modified chitosan Q groups wherein the organic acyl groups appended from the modified alcohol or amino group of the polysaccharide are independently a straight or branched chained alkanoyl group. Most preferred are such modified chitosan Q groups wherein the polarity resulting from the modification of chitosan alcohol or amino groups with organic acyl groups allows the modified chitosan to absorb both lipids and water and to form a substantially homogenous gel with lipids and water.

Most preferred are the compounds as set forth above, wherein the Q group is a chitosan compound modified with a sufficient number of organic acyl groups to cause the modified chitosan to absorb or associate both lipids and water and to form a substantially homogenous gel with oil and water. The number of organic acyl groups present on the modified chitosan chains are present in a molar ratio from 1 to 8 times the number of the molar ratio of esterified lipase inhibitor alcohol groups, and more preferably a ratio from 2 to 5 times, and most preferably a ratio of from 3 to 4 times the number of esterified lipase inhibitor alcohol groups.

Preparation of Compounds

The lipase inhibitor compounds, polymer moieties and bridging groups of the present invention may be synthesized or readily obtained from commercially available sources. Polymer bridging groups, bridge coupling processes and compound purification methods are described and referenced in standard textbooks, particularly the coupling of alcohol groups via diether bridges, ether/ester bridges, ether/ketone bridges and the like. Standard polymer textbooks reference typical bifunctional bridging groups and coupling procedures.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups may be protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Lipase inhibitor moieties having a free hydroxy group such as tetrahydro-esterastin (3,5-hydroxy-2-hexadeca-7,10-dienoic 1,3-lactone), 3,5-dihydroxy-2-hexylhexadeca-7,10-dienoic 1,3-lactone, 3,5-di-hydroxy-2-hexylhexadecanoic 1,3-lactone, and the like, are easily coupled to a polymer moiety having free hydroxy groups such as cellulose, chitosan and other polysaccharides having free hydroxyl groups. One or both of the lipase inhibitor moiety and the polymer moiety may be derivitized to form part of the linking bridge prior to reacting with the other moiety. For example, the lipase inhibitor molecule may be condensed with a dihalide group or a terminal halide terminal acyl (acyl group may be protected with an acid group) to form an ether or ester linkage and then condensed with a polymer moiety having a free hydroxyl group or free amino group by methods shown in polymer chemistry. In one procedure a polymer moiety such as chitosan can be reacted with a compound such as a halomethylbenzoic acid ester, $C_2$ to $C_{20}$ n-haloalkanoic acid, $C_2$ to $C_{20}$ n-alkanoic acid ester or the like, and optionally de-esterified to present a free acid group which may be reacted to form an ester, ketone, carboxamide or the like with the derivitized or underivatized lipase inhibitor moiety. In one preferred aspect of the invention, the amino or alcohol groups of the polysaccharide moiety, such as chitosan, is reacted with one or more types of n-haloalkanoic acid (or an acyl ester derivative) such as n-bromohexanoic acid, n-chlorolauric acid in a molar ratio 1:1 to 1:10, or the like, sufficient to attach an organic acyl side chain to 1 to 10%, preferably from 1 to 5% and more preferably from 2 to 4%, of the free alcohol groups, amino groups or alcohol and amino groups on the polysaccharide chain to provide an organic acyl group modified polysaccharide, such as an organic acyl group modified chitosan derivative. In such case, the n-haloalkanoic acid, or other halo derivative organic acyl group, etherizes free hydroxyl groups, replaces a hydrogen atom on an amino group, or forms a ketone with an acid group or a previously modified polysaccharide compound, and the resulting intermediate can then be reacted with the lipase inhibitor to form an ester group with a free alcohol group, replace a hydrogen atom on a amino group to form a carboxamide, and the like. Particularly preferred polymer moieties to be modified are polysaccharides having multiple free hydroxyl groups or amino groups for coupling, such as chitosan or a chitosan that has optionally been sulfonated to render the lipase moiety itself a lipase inhibitor compound. Etherification, amination and ketone formation procedures are well-known in the art and well within the routine skill of the ordinary practitioner. Further, other bridging groups and the techniques for binding a compound having a reactive functional group to a polymer moiety are well-known in the art. The preferred compounds also include their pharmaceutically acceptable isomers, hydrates, solvates, salts and prodrug derivatives.

The bridging group refers to a bifunctional chain or spacer group capable of reacting with one or more functional groups on a lipase inhibitor compound and then react with a second same or different functional group on a polymer compound in order to form a linked structure or conjugate between the two compounds. The bond formed between the bridging group and each of the two compounds is preferably of a type that is resistant to cleavage by the digestive environment, except that the lipase inhibitor may optionally be cleavable by a digestive lipase. In one aspect, the bridging group is of the formula X—R—X, wherein R is a member selected from a straight-chained or branched alkyl group, a straight-chained or branched alkenyl group, a straight-chained or branched alkynyl group, a mono acyl group, a diacyl group and the like, and X is a functionally reactive group such as a halogen or an acid group, preferably on X is bromo and the other is an acyl or acyl ester group, which react under the special reaction conditions as described hereinafter. Particularly preferred bridging groups form a terminal ether or a terminal amino alkyl bond with the polysaccharide and an acyl ester or carboxamide bond with the lipase inhibitor.

Examples of alkylene dichloride bridging group forming compounds are dichloromethane, 1,2-dichloroethane, 1,2- and 1,3-dichloropropane, 1,2-, 1,3- and 1,4-dichlorobutane, 1,2-bromochloroethane, 1,2-and 1,3-bromochloropropane, and the like.

Examples of acyldichloride bridging group forming compounds are oxalic acid dichloride, malonic acid dichloride, succinic acid dichloride, glutaric acid dichloride, adipic acid dichloride, pimelic acid dichloride, suberic acid dichloride, fumaric acid dichloride, malic acid dichloride, glutamic acid dichloride, terephthalic acid dichloride, isophthalic acid dichloride, and the like.

Examples of haloacyl bridging groups include chloromethylbenzoic acid or an ester thereof, 3-bromopropanoic acid, 2-chloroacetic acid, 6-bromohexanoic acid or an ester thereof, 12-bromododecanoic acid or an ester thereof, other n-haloalkanoic acids or esters thereof, and the like.

Other such bridging group reagents are compounds such as epichlorhydrin, phosphorus oxychloride, and diphosphoryl tetrachloride, and the like.

Preferred bridging groups terminated with at least one bromo or chlorine group and the other terminus is an acyl group or an acyl derivative. Even more preferred bridging groups are n-halo(preferably n-bromo)-$C_4$-$C_{20}$ (preferably $C_6$-$C_{14}$) alkanoic acids or esters thereof. The reaction is reacting the bridging group with the polysaccharide under either etherification or amino alkylation conditions in a substantially water immiscible organic solvent, such as THF substantially 1:1 to 1:10 molecular ratio of polysaccharide chain to bridging group reactant. The reaction may proceed at the interface between the two immiscible solutions, or in solution, to provide a condensation and produce the polysaccharide derivative or analogue. It has been discovered that this reaction at the interface of the organic solution and the aqueous solution imparts a specificity to the reaction for primary alcohol groups of the polysaccharide. A miscible solvent such as THF, an ether or the like, favors alkylation of the amino groups. It should be understood that equivalent reactants such as diepoxides and balohydrocarbyloxiranes such as epichlorohydrin also react in the process to provide new and useful ether bridges.

By appropriate selection of the type of bridging group reactant and reaction conditions, different structural groups with various chemical properties can be incorporated into the resulting bridge and various types of lipase inhibitors can be connected to a nonabsorbable polymer moiety, such as a polysaccharide, and preferably to chitosan or modified chitosan. Reaction temperatures and other reactions conditions, as well are reactant proportions are well within the skill of the ordinary polymer chemist practitioner in view of the present description of the invention. Other groups and modifications will be apparent to one of ordinary skill in the art from the above discussion.

The lipase inhibitor functionality of the coupled lipase inhibitors may be determined by well-known lipase inhibitor assays. A therapeutically effective amount of the bound lipase inhibitor may be administered to a patient. Additional fat binding polymers may optionally be added to the composition.

The following non-limiting reaction Schemes I, II, III and IV illustrate preferred embodiments of the invention with respect to making compounds according to the invention.

Scheme I

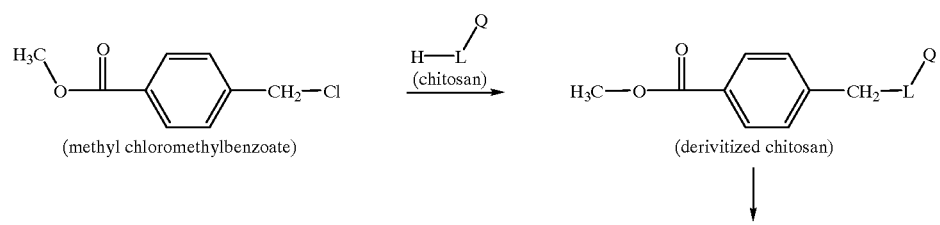

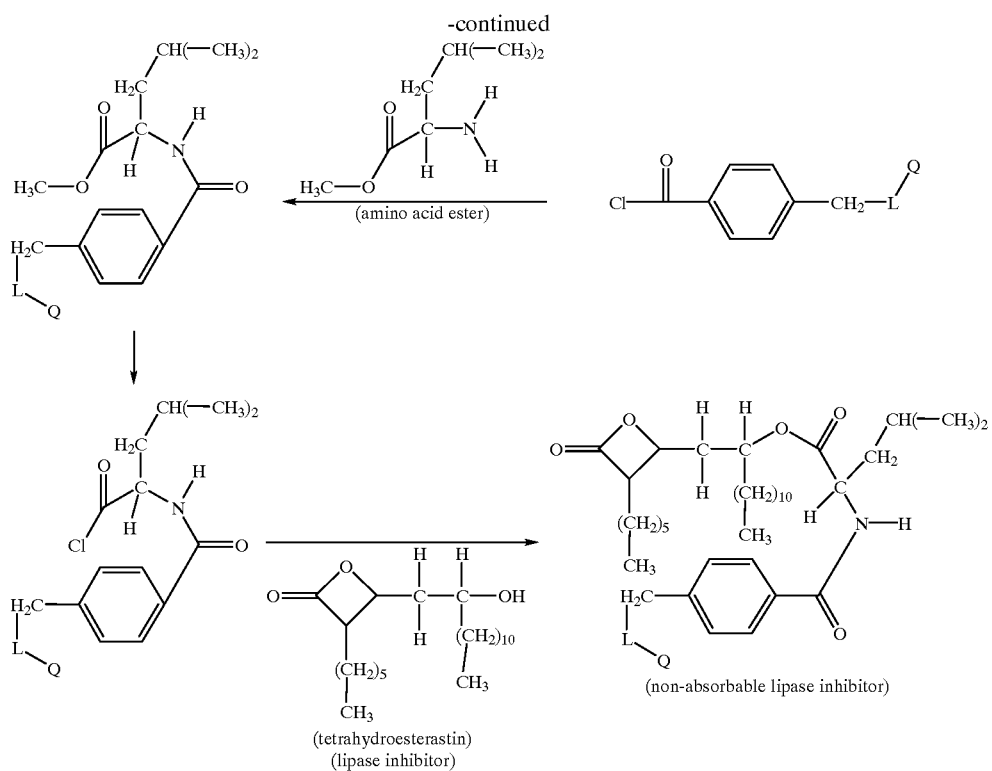
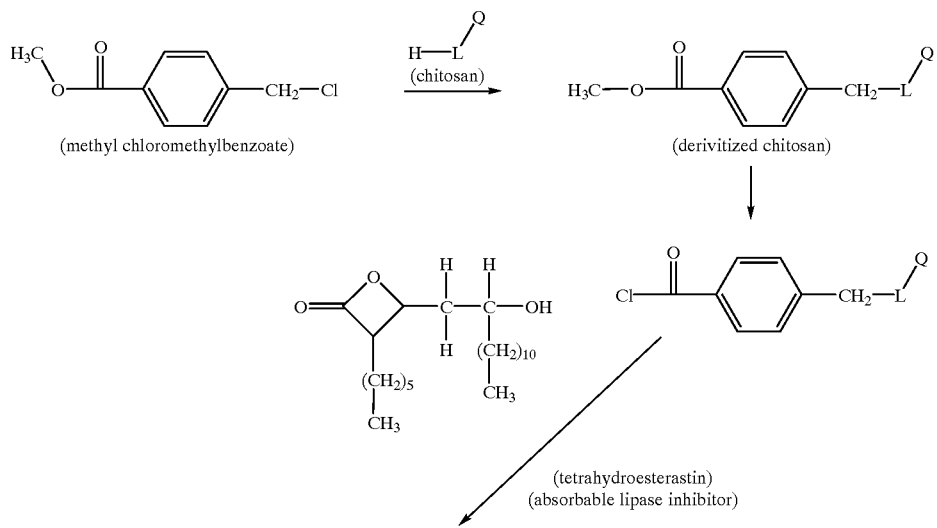
Scheme II

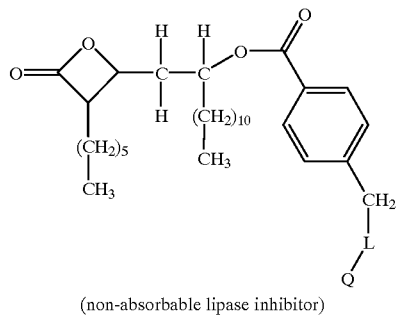
(non-absorbable lipase inhibitor)
Scheme III
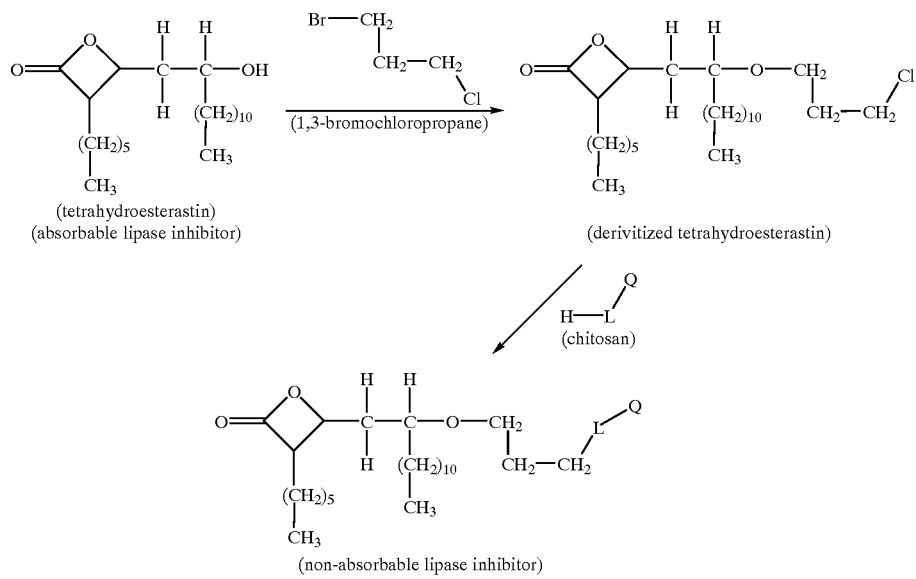
Scheme IV
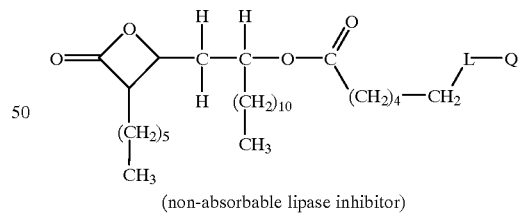
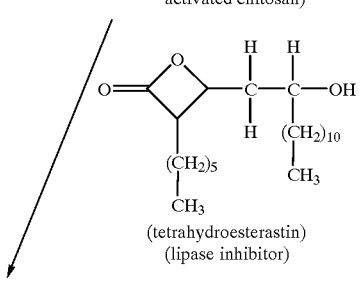
Therefore, in a preferred aspect the invention provides a method for producing a compound of claim 1, comprising reacting a compound of the formula:
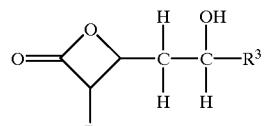

with a compound of the formula

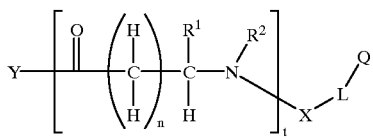

wherein L is —O— or —NH—, t is 0 or 1 and Y is a leaving group for an etherification or esterification reaction with the hydroxy group to produce a compound of the formula:

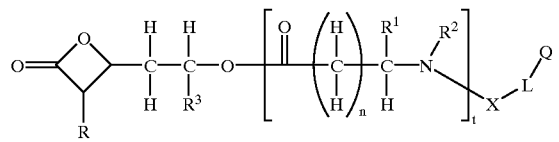

or a salt thereof.

Pharmaceutical Compositions and Edible Compositions

In one aspect, the present invention provides a sports drink, snack, nutrient supplement, food or power which may be formulated to contain a lipase inhibiting therapeutically effective amount of the lipase inhibitor composition according to the invention.

In another aspect the present invention relates to pharmaceutical compositions comprising a lipase inhibiting effective amount of at least one lipase inhibitor which is coupled to a digestively non-absorbable moiety. Preferred are such pharmaceutical compositions comprising an effective amount of a lipases coupled to a non-absorbable biocompatable, pharmaceutically acceptable polymer moiety, such as a polysaccharide, wherein the lipase is essentially non-absorbable by the digestive system of an animal such as a dog, cat, non-human primate or humans. The pharmaceutical composition can be administrated to a patent prior to or within one hour of consuming a fat-containing meal to prevent absorption of up to one-third of the dietary fat consumed at the meal.

In still another aspect, the present invention relates to a method for treating adiposity or obesity by administering to a patient before a fat-contain meal, or up to one hour after such a meal is consumed, an amount of at least one lipase inhibitor which is bound to a non-absorbable polymer moiety in an amount effective to inhibit the absorption of up to one-third of the dietary fat in such a meal. In particular, a preferred method comprises administering at one lipase inhibitor which is a member selected from the group consisting of esterastin, tetrahydro-esterastin (3,5-hydroxy-2hexadeca-7,10-dienoic 1,3-lactone), 3,5-dihydroxy-2-hexylhexadeca-7, 10-dienoic 1,3-lactone, 3,5-di-hydroxy-2-hexylhexadecanoic 1,3-lactone, and the like, wherein such lipase inhibitor is coupled to a non-absorbable biocompatable, pharmaceutically acceptable polymer moiety, such as a polysaccharide, to render the lipase non-absorbable by the digestive system of an animal such as a dog, cat, non-human primate or humans. Particularly preferred polysaccharides are at least one member selected from the group consisting of dextrans, molecular microcrystalline cellulose, wheat bran, oat bran, defatted rice germ, alginic acid, pectin, amylopectin, chitin, crude cellulose, argar, chitosan and the like. Particularly preferred bound lipase inhibitors are lipase inhibitors bound via a derivatized nitrogen, acid or alcohol group to a derivatized alcohol, acid or amino group on the polymer moiety. Preferred bound polymer moities are derivatized to have an excess of acyl organic acid side chains which are adequate to cause the compound to absorb both oil and water or associate with both oil and water to provide a substantially homogeneous gel. A ether bond or alkylamino bond at one bridge terminus and an acyl ester or carboxamide bridge terminus connecting the lipase inhibitor and the polysaccharide moiety is preferred which is derived from an alcohol group on the lipase and an alcohol or amino group on the polysaccharide moiety, respectively reacting with a bridging group is the preferred coupling of the lipase inhibitor to the moiety.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

Numerous methods are useful for the preparation of the salts described above and are known to those skilled in the art. For example, free acid or free base forms of a compound of one of the above compounds can be reacted with one or more molar equivalents of the desired acid or base in a solvent or solvent mixture in which the salt is insoluble, or in a solvent like water after which the solvent is removed by evaporation, distillation or freeze drying.

Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous, acid/base reaction, or enzymatic, within the organism to release the active drug. Prodrugs are variations or derivatives of the compounds of this invention which have groups cleavable under digestive system conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, digestive compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A.R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. Accordingly, it may be necessary for the therapist to titer the dosage and modify the means of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally in an effective amount within the dosage range of about 10 to 400 mg/kg, preferably about 20 to 200 mg/kg and more preferably about 20 to 50 mg/kg per fat containing meal on a regimen in a single or 2 to 4 divided daily doses. A preferred dosage is an amount (e.g. about 20 to 40 mg/kg) that has a similar lipase inhibiting effect to the lipase inhibition of 120 mg (approximately 1–2 mg/kg dosage) of orally taken Orlistat. The determination of such equivalent lipase inhibition can be determined via well-known lipase inhibition assays, and may be either an in vivo assay, an in vitro assay, or both. The fat absorption properties of the lipophilic lipase inhibitor of the invention can be observed by comparing the amount of anal oil discharged in a patient taking an lipase inhibitor equivalent amount of the lipase inhibitor according to the invention as compared to a patient taking only Orlistat. The grooming of mice with anal oil is one comparison as compared to Orlistat or the actual comparison of anal discharge in animals or patients also will show a reduction in the amount of oily anal discharge when a lipophilic lipase inhibitor according to the invention is administered.

Typically, for a unit dose form, about 500 mg to 2 g of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In certain aspects of this invention, compounds are provided which are useful as diagnostic reagents to determine lipase activity. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired lipid or fat absorption such as obesity, hyperlipaemia, atherosclerosis and ateioscherosis disorders of the blood coagulation process in mammals, or for stabilizing fats by preventing lipase function in stored fat products and samples. Optionally, the methods of this invention comprise administering the pharmaceutical composition in combination with an additional therapeutic agent such as an anticholesterol agent, appetite suppressant, metabolic stimulant and the like.

The preferred compounds also include their pharmaceutically acceptable isomers, hydrates, solvates, salts and pro-drug derivatives.

In one embodiment the present invention provides a pharmaceutical composition comprising at least one pharmaceutically acceptable carrier excipient and an amount of at least one of the above described compounds according to the invention in a therapeutically effective amount with respect to limiting or preventing the absorption of some dietary fat. In a preferred embodiment, the pharmaceutical composition comprises a therapeutically effective amount of slow-release lipoprotein lipase, preferably from a microbial or plant source, which selectively hydrolyzes terminal triglyceride groups in combination with an oil absorbing effective amount of polysaccharide such as chitosan, wherein the lipoprotein lipase is present in a ratio of less that 25% with respect to the oil absorbing polysaccharide.

In another embodiment the present invention provides a pharmaceutical composition comprising at least one pharmaceutically acceptable carrier excipient, an amount of at least one of the above described compounds according to the invention in a therapeutically effective amount with respect to limiting or preventing the absorption of some dietary fat, and an oil absorbing effective amount of polysaccharide such as chitosan, wherein such lipase inhibitor is selectively effective to inhibit lipases other than lipases involved in the hydrolysis of terminal triglyceride groups and such lipase inhibitor does not substantially inhibit the absorption of vitamins A, D and E.

In another embodiment the present invention provides a method of using such compounds and pharmaceutical compositions as therapeutic agents for disease states in a mammal having at least one disorder that is due to undesired absorption of dietary fat or for reducing the effective caloric intake of a mammal who consumes dietary fat, which method may be useful in the treatment of undesired weight gain or obesity.

The compounds of this invention also find utility as intermediates for producing therapeutic agents or as therapeutic agents for disease states in mammals which have disorders that are due to undesired absorption of dietary fat. Methods for making starting materials may be found in U.S. Pat. No. 4,931,463, which is incorporated fully herein. Preferred oxetanones of the invention are compounds wherein R is methyl, ethyl, propyl, hexyl, decyl, hexadecyl, allyl and benzyl, and most preferably hexyl; $R^1$ is hydrogen, methyl, ethyl, propyl, 2-butyl, isobutyl, benzyl and methylthio-ethyl, most preferably, hydrogen or isobutyl; $R^2$ is hydrogen, methyl or ethyl, most preferably hydrogen; n is 0 or 1, and when t is 1, then X is preferably attached to N via an amino acid, such as valine, alanine and the like, preferably alanine; and $R^3$ is preferably a straight or branched chained $C_{1-17}$-alkyl group which is saturated or optionally interrupted by up to eight double or triple bonds, or $R^3$ is a straight or branched chained $C_{1-17}$-alkyl group which is saturated or optionally interrupted by one or more members selected from the group consisting of an oxygen atom, a sulfur atom, a sulfonyl group or a sulfinyl group or $R^3$ is a straight or branched chained $C_{1-17}$-alkyl group which is saturated or optionally interrupted by up to eight double or triple bonds and is interrupted in a position other than alpha to an unsaturated carbon atom by one or more members selected from the group consisting of an oxygen atom, a sulfur atom, a sulfonyl group or a sulfinyl group atoms.

The compounds produced according to the present invention, particularly, the modified polysaccharides, may also be used as intermediates in the formation of compounds that may be administered in combination or in concert with other therapeutic or diagnostic agents, however, they may be useful as oil absorbing polymers that are capable of dispersing in water after oil absorption. Such may be useful food additives. In certain preferred embodiments, the compounds produced by the intermediates according to the present invention may be co-administered along with other compounds typically prescribed for these conditions according to generally accepted medical practice such as other dietary maintenance medicaments and for diseases related to or impacted by the absorption of dietary fat. The compounds produced from the intermediates according to the present invention may act in a synergistic fashion with other such medicaments. Such compounds may also allow for reduced doses of other cholesterol inhibiting, appetite inhibiting and metabolic stimulating medicaments, and the like. Such compounds can be utilized in vivo, ordinarily in mammals such as primates, (non-human and humans), sheep, horses, cattle, pigs, dogs, cats, rats and mice, or in vitro.

The starting materials used in above processes are commercially available from chemical vendors such as Aldrich, Sigma, Lancaster, TCI, and the like, or may be readily synthesized by known procedures, for example, by using procedures such as indicated above.

Reactions are carried out in standard laboratory glassware and reaction vessels under reaction conditions of standard temperature and pressure, except where otherwise indicated, or is well-known in literature available in the art. Further, the above procedures of the claimed invention processes my be carried out on a commercial scale by utilizing reactors and standard scale-up equipment available in the art for producing large amounts of compounds in the commercial environment. Such equipment and scale-up procedures are well-known to the ordinary practitioner in the field of commercial chemical production.

During the synthesis of these compounds, amino or acid functional groups may be protected by blocking groups to prevent undesired reactions with the amino group or acid group during certain procedures. Procedures for such protection and removal of protecting groups are routine in this art and well-known to the ordinary practitioner in this field.

Four non-limiting exemplary synthesis schemes were shown above, which are each a preferred embodiment of the invention, comprise the process steps outlined above which may also include further initial starting steps such as those set forth in J. Med. Chem., Vol. 15, No. 8 (1972) or further processing steps which modify the amino group to comprise a desired functional group such as groups described in the lipase inhibiting field. Amino coupling reactions are well-known in the art. Moreover, specific steps that are set forth in the preferred embodiment reaction scheme described above. The reaction products are isolated and purified by conventional methods, typically by solvent extraction into a compatible solvent. Preferred solvents are lower alkane ethers and alcohols; ethyl ether and isopropyl alcohol are preferred for solvent extraction or recrystallization procedures. Esters of carboxylic acid side groups may be formed that permit selective separation of the R and S enantiomers by solvent extraction or recrystallization. D-alaninol is the preferred enantiomer resolving agent, but other resolving agents or analogous procedures may be used, e.g., tartaric acid derivatives and the like. The products may be further purified by column chromatography or other appropriate methods.

Enantiomeric Resolution and Acid Salt Formation

As is clear from the above formulae and the discussion above, by using the above reactions racemic chromane acetic acid is obtained which may optionally be resolved to produce a racemic mixture enriched in either the R or S enantiomers or completely resolved into a substantially pure composition of one of the enantiomers. The literature in this field describes examples of conventional processes whereby the enantiomers may be resolved.

Coupling Reaction of the Hydrochloride Salt Intermediate Compounds

The above compounds produced according to the above invention may be isolated and further reacted to substitute a desired group for one or more of the hydrogen atoms on an amino group, on a free hydroxyl group or on a free acyl group by a coupling reaction with the desired group.

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of undesired fat absorption the compounds of this invention may be utilized in compositions such as tablets, capsules or elixirs for oral administration, sterile solutions or suspensions, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences,* Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by oral tablets, capsules or other unit dose mechanisms, such as liquids, other methods of administration are also anticipated such as in food stuffs, employing a variety of dosage forms. The compounds of this invention are desirably incorporated into food articles which may include fats to prevent their absorption.

The compounds of this invention may also be coupled with suitable polymers to enhance their therapeutic effects. Such polymers can include lipophilic polymers, such as polysaccharides and the like.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For routes of administration, the lipase inhibitor activity, in view of the amount of fat consumed, must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

Typically, about 500 mg to 3 g of a lipase inhibitor compound or mixture of lipase inhibitor compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained. The addition, one or more other therapeutic ingredients such as a fat absorbing polysaccharide or fiber, a fat-specific lipase inhibitor or lipase, as well as other dietary agents may be utilized in therapeutically effective amounts.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as The compounds of this invention can be utilized in vivo, ordinarily in mammals such as non-human primates, humans, sheep, horses, cattle, pigs, dogs, cats, rats and mice, or in vitro.

The following non-limiting examples are provided to better illustrate the present invention.

EXAMPLE 1

10 grams of low viscosity chitosan is dissolved in a 500 milliliter flask equipped with a stirrer thermometer and electrical heater, in a mixture of 190 g of dimethylsulfoxide and 10 g of paraformaldehyde, at 50° C. At this temperature, after the addition of 0.1 g of finely powdered sodium hydroxide, a solution of 400 mg of p-chloromethyl benzoic acid methyl ester in 10 g of dimethylsolfoxide is added over a period of about 30 minutes. The mixture is stirred for four hours at 50° C. The reaction mixture is cooled to room temperature, then poured into ethanol while the latter is being stirred vigorously. The solid is suction filtered, suspended repeatedly in ethanol until all the soluble substances are removed to yield a crude product. The crude product is stirred in an aqueous basic 1 N sodium hydroxide ethanol solution, which is then acidified with HCl until neutral pH for chitosan. The solid is washed twice with cold ethanol and cold water, and the solid is then dried to yield about 10 grams of ether functionalized chitosan. Analysis indicates that from 1% to 3% of the free hydroxyl groups on the chitosan polymeric backbone are etherified by the entry of the p-methylbenzoic acid group.

EXAMPLE 2

A colorless power of 3,5-dihydroxy-2-hexyl-hexadecanoic 1,3-lactone (6 g, produced as described on pages 11 and 12 of U.S. Pat. No. 4,202,824) is dissolved in 500 mL of THF to which is added Boc-(L) 2-amino-4-methylpentanoic acid chloride (3 g, Boc-(L)-Leucine). The reaction mixture is stirred and heated to reflux until HPLC indicates that the esterification is essentially complete. The organic phase is evaporated and the residue purified by chromatography on silica gel with toluene-ethyl acetate to yield 5-[Boc-(L) 2-amido-4-methylvaleryloxy]-2-hexyl-hexadecanoic 1,3-lactone (6 g).

EXAMPLE 3

The BOC group of the product (6 mg) of Example 2 is removed by hydrogenation at room temperature in 120 mL of THF in the presence of 10% Pd/C. After hydrogenation is completed, the catalyst is filtered off and the filtrate is evaporated to yield a crude free amino group product, which is taken up in 100 mL of THF. The functionalized chitosan product produced in Example 1 is taken up in 200 mL of THF and stirred while the crude free amino product is added dropwise at room temperature. The mixture is gradually heated to 40° C. with stirring until HPLC indicates the formation of the carboxamide linked product. Yielded is 5-[2-{(4-chitosan methyl ether) benzoylamido}-4-methylvaleryloxy]-2-hexyl-hexadecanoic 1,3-lactone (about 15 grams).

EXAMPLE 4

To a 1 liter flask was added 20 g of chitosan that had been dissolved in 350 mL of DMF (N,N-dimethylformamide), with stirring and the temperature was raised to 50° C. A mixture of 0.2 g of NaOH and 1 g of 6-bromohexanoic acid in 20 mL of DMF was added slowly over 30 minutes with stirring. The reaction mixture was stirred at 50° C. for 4 hours. The reaction mixture was cooled to room temperature and poured into 500 mL of ethanol. The solid is suction filtered and washed three times with cold ethanol. The crude precipitate was treated in 1N NaOH ethanol solution for 3 hours, then the pH was reduced to neutral by the addition of 1N HCl. The solid was washed with cold ethanol and $H_2O$ (4:1 ratio) 3 times and dried to provide 19.7 g of functionalized chitosan.

EXAMPLE 6

To 200 mL of THF (tetrahydrofuran) was added 9 g of the functionalized chitosan from Example 5, with stirring. To this mixture was added 10 mmol of HBTU (1H-benzotriazolium-1-[bis, (dimethylamino)methylene]-hexafluorophosphate(1-)-3-oxide) dissolved in 10 mL of DMF with stirring over a 10 minute period. Tetrahydrostatin L-leucine ester (about 525 mg) dissolved in 100 mL of THF was added dropwise with stirring. The pH was then adjusted to about 8.5 by the addition of DIEA (disopropylethylamine) and the mixture was stirred at room temperature overnight. The reaction mixture was reduced in volume by evaporated under vacuum to about 50% volume and 500 mL of hexane was added. The mixture was filtered and the solid cake was washed with cold hexane three times and then with a cold ethanol/water (3:1) solution 3 times. The filter cake was dried under a lyophilizer to yield 9.3 grams of final product 2S, 3S, 4S [2-{(hexanoic acid modified chitosan 6-hexanoylamido}-4-methylvaleryloxy]-2-hexyl-hexadecanoic 1,3-lactone (Compound A).

EXAMPLE 7

To 200 mL of THF was dissolved with stirring 10.65 g of the functionalized chitosan from Example 5, above, followed by 2 mmoles of HBTU. The mixture was stirred together for 15 minutes and then 350 mg of 2S, 3S, 4S 2-hexyl-4-hydroxy-hexanoic 1,3 lactone that was dissolved in 30 mL of THF (tetrahydrofuran) was added. The pH was adjusted to about 8.5 by the addition of DIEA and the mixture was stirred overnight. The reaction mixture was filtered and the solid was washed with cold hexane 3 times and then washed 3 times with a cold ethanol/water (3:1) mixture. The filter cake was dried under a lyophilizer to yield 11.1 g of final product 4-[{(hexanoic acid modified chitosan 6-hexanoyloxy}-2-hexyl-hexadecanoic 1,3-lactone (Compound B).

BIOLOGICAL AND OTHER PROPERTIES ASSAY EXAMPLES

EXAMPLE 8

Lipase inhibition assays were performed essentially as follows using each of Compounds A and B.

A 1 L stock solution of 1N NaOH was made and a 500 mL stock solution of 0.025 N NaOH was made by diluting a portion of the stock 1N solution. Also a stock solution of 0.2 N HCl was made. A 100 mL TRIZMA solution (from Aldrich Lipase Assay Kit Cat. No. 800B) was diluted with 100 mL of denatured EtOH and 300 mL of water to form a 500 mL TEW solution. Compound A from Example 6 (100 mg) was added to a portion of the 0.2 N HCl stock solution and diluted to a final volume of 300 mL with the same HCl stock solution to form a compound A stock solution. Compound B from Example 7 was added to a portion of the 0.2 N HCl stock solution and diluted to a final volume of 80 mL with the same HCl stock solution to produce a compound B stock solution. Aldrich Lipase PS Standard (human lipase 3 mL×3) Aldrich Product No. 8054 was diluted with isotonic saline solution to a 25 mL volume (Lipase #1 solution). Likewise Aldrich Pork Pancreas Lipase [EC 3.1.1.3] Product No. 32313 was diluted to a final volume of 25 mL with isotonic saline (Lipase #2 solution). Aldrich Sigma Lipase Substrate Standard Cat. Product No. 62314 (3×100, 300 mL) was obtained to use as the lipid source.

In a 500 mL beaker equipped with a heat source and a magnetic stirrer was added 100 mL of distilled water, 10 mL of TEW solution, 10 mL of Sigma Lipase Substrate and a 20 mL sample (sample control was 20 mL of the stock 0.2 N HCl solution, sample A was 20 mL of the compound A stock solution, and sample B was 20 mL of the compound B stock solution). The pH was adjusted to about 8 with 1N NaOH using a pH meter, whose reading was noted and recorded as a baseline reading after the pH adjustment. The temperature was brought to 37.5° C. and 1 mL of either Lipase #1 or Lipase #2 was added and a timer was started for 30 minutes. The mixture was stirred and the temperature maintained between 35° C. and 37° C. At the end of the time period, the mixture was stirred and triturated with 0.025 N NaOH. The volume of NaOH solution used to return to the baseline pH reading was noted and recorded. The percent inhibition by the Sample A or Sample B was calculated by subtracting the volume of NaOH used to return from baseline pH for either of Sample A or Sample B from the average volume of NaOH used to return from baseline pH for the control sample (three runs), the difference is divided by the average volume of NaOH used to return to baseline pH for the control sample, and the result was multiplied by 100% to obtain the percent inhibition of Sample A or Sample B (two runs each).

Each of Sample A and B showed a percent inhibition of about 50% with respect to the control for each of Lipase #1 and Lipase #2.

EXAMPLE 9

Oil binding assay were performed using each of Compounds A and B using the procedures essentially as follows.

Six controls were obtained by adding Star Brand Olive Oil (extra virgin light colored olive oil) to 4 or 7 mL sample bottles, which were photographed at a distance of 10 inches by using an IZONE POLAROID camera as follows. Control 1 was obtained by adding 3 mL of olive oil to a 7 mL bottle, which showed the clear but light reflective oil. Control 2 was obtained by adding 3 mL of olive oil to a 7 mL bottle and adding 10 drops of McCormick Schilling Red Food Coloring (RFC), which showed the oil insoluble food color at the bottom of the bottle and floating on top of the red food coloring is the 3 mL of light reflective olive oil. Control 3 was obtained by adding 3 mL of olive oil to a 7 mL bottle and adding 3 mL of water followed by 5 drops RFC, which showed of the clear separation of the red aqueous layer on the bottom of the bottle and floating on top was the light reflective olive oil. Control 4 was obtained by adding 1.5 g of olive oil to 1 g of chitosan (Natural Max Brand, greater than 90% deacylated chitin) and the two were mixed with a stirrer, followed by the addition of 4 mL of water and 5 drops of RFC, which showed the oil tightly bound to the chitosan in the bottom of the bottle, upon which was floating the aqueous red food color layer (a clean red meniscus with substantially no floating oil was observed). Control 5 was obtained by adding 1.5 g of olive oil to 1 g of cellulose (Avicel) and the two were mixed with a stirrer, followed by the addition of 4 mL of water and 5 drops of RFC, which showed some oil bound in the bottom to the cellulose, upon which was floating the aqueous red food color layer, further upon which was floating a clear layer of oil, about ¾ mL (a clear floating oily layer meniscus was observed to show that cellulose does not tightly bind an excess of its weight in oil. Control 6 was obtained by adding 8 g of olive oil to 1 g of chitosan and the two were mixed together with a stirrer, followed by the addition of 1 mL of water and 5 drops of RFC, which shows an hour-glass shape of oil bound by chitosan surrounded in the middle of the bottle at the narrow point with the aqueous red food color solution (chitosan binds oil and substantially excludes water from the bound mixture).

For comparison with Control 4 (oil/chitosan 1.5/1 ratio) each of Compounds A and B were mixed with oil in the same ratio(oil/compound 1.5/1 ratio, green food coloring was added to the aqueous portion of the compound A sample bottle and blue food coloring was added to the aqueous portion of the compound B sample bottle). The same results occurred with each of Compounds A and B as for the chitosan Control 4, in that the oil is bound tightly at the bottom of the bottle and there is substantially no floating oil, i.e., the meniscus for each is a clean green and blue meniscus. However, Compound B appeared to perhaps bind the oil more tightly than either chitosan or compound A.

For comparison with Control 6 (oil/chitosan 8:1 ratio and 1 mL of aqueous solution with food coloring), compound B was added to 8 times its weight of oil and stirred to a uniform consistency. The 1 mL of water was added and 5 drops of red food coloring were added. Upon mixing, the oil and compound B swelled to form a grainy gel-like consistency and uniformly absorbed the 1 mL of aqueous food coloring solution to form a homogenous layer which was present even after 24 hours. This shows that compound B has the ability to bind oil and then absorb at least its weight in water to form grainy gel-like homogeneous mixture, and continues to tightly bind the oil while being hydrated with water.

In view of the above description it is believed that one of ordinary skill can practice the invention. The examples given above are non-limiting in that one of ordinary skill in view of the above will readily envision other permutations and variations on the invention without departing from the principal concepts. Such permutations and variations are also within the scope of the present invention.

What is claimed is:
1. A novel oxetanone derivative of the formula:

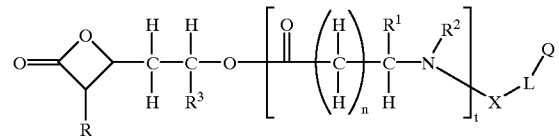

wherein:
　t is an integer from 0 to 1
　X-L-Q is an ether or amino linkage wherein:
　　X of the ether or amino is a linking group,
　　L is —O— or —NH—, and
　　Q of the ether or amino linkage is a polysaccharide of a sufficient molecular weight or property that such polysaccharide is not absorbed by the digestive system of a mammal such as a dog, cat, non-human primate or a human primate;
　R is a member selected from the group consisting of:
　　a straight or branched chained $C_{1\text{-}17}$-alkyl group which is saturated or optionally substituted by up to eight double or triple bonds;
　　a straight or branched chained $C_{1\text{-}17}$-alkyl group which is saturated or optionally substituted by one or more members selected from the group consisting of an oxygen atom, a sulfur atom, a sulfonyl group or a sulfinyl group;
　　a straight or branched chained $C_{1\text{-}17}$-alkyl group which is saturated or optionally substituted by up to eight double or triple bonds and is substituted in a position other than alpha to an unsaturated carbon atom by one or more members selected from the group consisting of an oxygen atom, a sulfur atom, a sulfonyl group or a sulfinyl group atoms;
　　phenyl substituted by 0–4 members selected from the group consisting of —$C_{1\text{-}6}$-alkyloxy-$C_{1\text{-}6}$-alkyl, —C$_{1-6}$-alkylthio-C$_{1-6}$-alkyl, —C$_{1-6}$-alkyl-OH and —C$_{1-6}$-alkyl-SH;
benzyl substituted by 0-4 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
biphenylene substituted by 0–6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C-$_{1-6}$-alkyl-SH;
phenoxyphenylene substituted by 0-6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
phenylthiophenylene substituted by 0–6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH; and
phenyl-C$_{1-6}$-alkyl-phenyl wherein 0–6 hydrogen atoms on one or more of the phenyl ring and —C$_{1-6}$-alkyl-group is/are replaced independently by a member selected from the group consisting of—C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
R$^1$ is a member selected from the group consisting of:
Hydrogen,
Ar,
Ar-C$_{1-5}$-alkyl and
C$_{1-10}$-alkyl substituted by 0-3 members independently selected from the group consisting of an oxygen atom, a sulfur atom, a sulfinyl group, a sulfonyl group, a-N(—R$^4$)— group, a —C(=O)—N(—R$^4$)— group, and a —N(—R$^4$)—C(=O)— group, wherein 0-3 carbon atoms of the C$_{1-10}$-alkyl group can be substituted independently by a member selected from the group consisting of a hydroxy group, thiol group, C$_{1-10}$-alkoxy group, a C$_{1-10}$-alkylthio group, a —N(—R$^5$,—R$^6$) group, a —C(=O)—N(—R$^7$, —R$^8$) group, and a —N(—R$^9$)—C(=O)—R$^{10}$ group;
R$^2$ is a member selected from the group consisting of:
hydrogen and C$_{1-6}$-alkyl, or R$^2$ taken with R$^1$ forms a 4-6 membered saturated ring containing 0-4 nitrogen atoms wherein the ring may be substituted by 0-4 R$^{11}$ groups;
R$^3$ is a member selected from the group consisting of:
a straight or branched chained C$_{1-17}$-alkyl group which is saturated or optionally substituted by up to eight double or triple bonds;
a straight or branched chained C$_{1-17}$-alkyl group which is saturated or optionally substituted by one or more members selected from the group consisting of an oxygen atom, a sulfur atom, a sulfonyl group or a sulfinyl group;
a straight or branched chained C$_{1-17}$-alkyl group which is saturated or optionally substituted by up to eight double or triple bonds and is substituted in a position other than alpha to an unsaturated carbon atom by one or more members selected from the group consisting of an oxygen atom, a sulfur atom, a sulfonyl group or a sulfinyl group atoms;
phenyl substituted by 0-4 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
benzyl substituted by 0-4 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
biphenylene substituted by 0-6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
phenoxyphenylene substituted by 0-6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
phenylthiophenylene substituted by 0-6 members selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH; and
phenyl-C$_{1-6}$-alkyl-phenyl wherein 0-6 hydrogen atoms on one or more of the phenyl ring and —C$_{1-6}$-alkyl-group is/are replaced independently by a member selected from the group consisting of —C$_{1-6}$-alkyloxy-C$_{1-6}$-alkyl, —C$_{1-6}$-alkylthio-C$_{1-6}$-alkyl, —C$_{1-6}$-alkyl-OH and —C$_{1-6}$-alkyl-SH;
R$^4$–R$^{10}$ are each independently a member selected from the group consisting of:
hydrogen and C$_{1-6}$-alkyl;
n is an integer of 0-3;
or a pharmaceutically acceptable isomer, and salt thereof.

2. A compound according to claim 1, wherein L is —NH—,
or a pharmaceutically acceptable isomer and salt thereof.

3. A compound according to claim 1, wherein X is the group —(C(=O))$_{0-1}$—X$_a$—, wherein X$_a$ is a member selected from the group consisting of:
a straight or branched chained divalent C$_{1-17}$-alkylene group which is saturated or optionally substituted by up to eight double or triple bonds;
a straight or branched chained divalent C$_{1-17}$-alkylene group which is saturated or optionally substituted by one or more members selected from the group consisting of:
an oxygen atom,
a sulfur atom,
a sulfonyl group,
a sulfinyl group,
a substituted or unsubstituted 6-10 member monocyclic or bicyclic aryl or heteroaryl group having from 1-4 ring hetero atoms selected from the group consisting of O, N, S,
a —NH— group, wherein the hydrogen atom may be replaced with a C$_{1-10}$ alkyl group
a —C(=O)— group,
a —NH—C(=O)— group, wherein the hydrogen atom may be replaced with a C$_{1-10}$ alkyl group and
a —C(=O)—NH— group, wherein the hydrogen atom may be replaced with a C$_{1-10}$ alkyl group
a straight or branched chained divalent C$_{1-17}$-alkylene group which is saturated or optionally substituted by up to eight double or triple bonds and is substituted in a position other than alpha to an unsaturated carbon atom by one or more members selected from the group consisting optionally substituted by one or more members selected from the group consisting of:
an oxygen atom,
a sulfur atom,
a sulfonyl group,
a sulfinyl group,
a substituted or unsubstituted 6-10 member monocyclic or bicyclic aryl or heteroaryl group having from 1-4 ring hetero atoms selected from the group consisting of O, N, S, a —NH— group, wherein the hydrogen atom may be replaced with a $C_{1-10}$ alkyl group a —C(=O)— group, a —NH—C(=O)— group, wherein the hydrogen atom may be replaced with a $C_{1-10}$ alkyl group and a —C(=O)—NH— group, wherein the hydrogen atom may be replaced with a $C_{1-10}$ alkyl group divalent phenylene or divalent naphthylene substituted on the ring structure by 0-4 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

divalent biphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

phenoxyphenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH;

divalent phenylthiophenylene substituted by 0-6 members selected from the group consisting of —$C_{1-6}$-alkyloxy-$C_{1-6}$-alkyl, —$C_{1-6}$-alkylthio-$C_{1-6}$-alkyl, —$C_{1-6}$-alkyl-OH and —$C_{1-6}$-alkyl-SH; and or a pharmaceutically acceptable isomer and salt thereof.

4. The compound of claim 3, wherein R is —$(CH_2)_{3-6}$—$CH_3$ and $R^3$ is a member selected from the group consisting of —$(CH_2)_{8-14}$—$CH_3$ and —$CH_2$—CH=CH—$CH_2$—CH=CH—$(CH_2)_{2-8}$—$CH_3$, or a pharmaceutically acceptable isomer and salt thereof.

5. The compound of claim 3, wherein R is —$(CH_2)_5$—$CH_3$ and $R^3$ is a member selected from the group consisting of —$(CH_2)_{10}$—$CH_3$ and —$CH_2$—CH=CH—$CH_2$—CH=CH—$(CH_2)_4$—$CH_3$, or a pharmaceutically acceptable isomer and salt thereof.

6. The compound of claim 3, wherein n is zero to provide compounds of the formula:

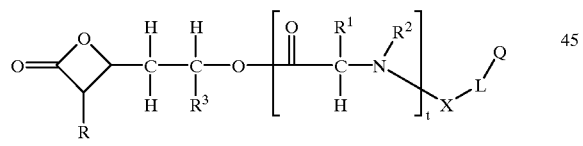

wherein:

X, L, t, Q, R, $R^1$, $R^2$ and $R^3$ are defined as in claim 2, or an isomer and salt thereof.

7. The compound of claim 6, wherein R is —$(CH_2)_{3-6}$—$CH_3$ and $R^3$ is a member selected from the group consisting of —$(CH_2)_{8-14}$—$CH_3$ and —$CH_2$—CH=CH—$CH_2$—CH=CH—$(CH_2)_{2-8}$—$CH_3$, or an isomer and salt thereof.

8. The compound of claim 6, wherein R is —$(CH_2)_5$—$CH_3$ and $R^3$ is a member selected from the group consisting of —$(CH_2)_{10}$—$CH_3$ and —$CH_2$—CH=CH—$CH_2$—CH=CH—$(CH_2)_4$—$CH_3$, or an isomer and salt thereof.

9. The compound of claim 6, wherein t is 0, or an isomer and salt thereof.

10. The compound of claim 3, wherein t is 0 or 1 and X is a member selected from the group consisting of:

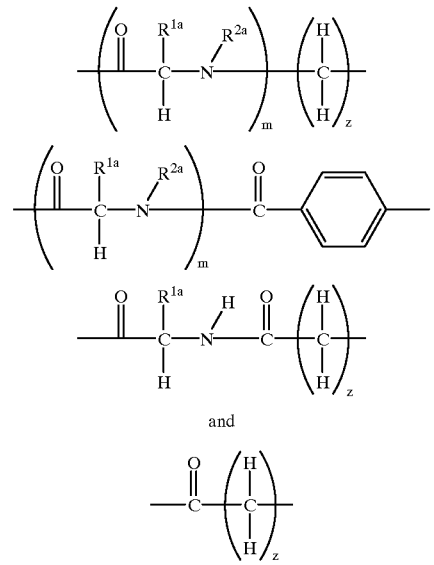

wherein $R^{1a}$ is independently defined the same as defined for $R^1$, $R^{2a}$ is independently defined the same as for $R^2$, m is a integer from 0 to 10, and wherein z is an integer from 1 to 20, or a pharmaceutically acceptable isomer and salt thereof.

11. The compound of claim 10, wherein X is a member selected from the group consisting of:

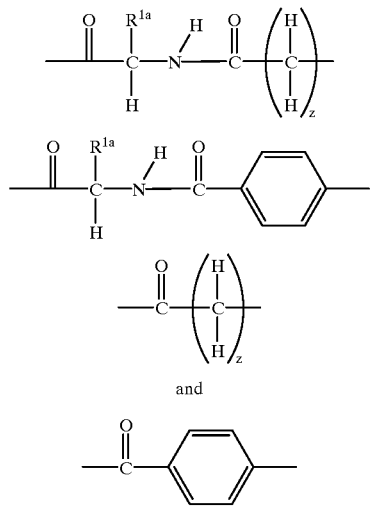

and wherein z is a integer from 0 to 10, or a pharmaceutically acceptable isomer and salt thereof.

12. The compound of claim 10, wherein X is a member selected from the group consisting of:

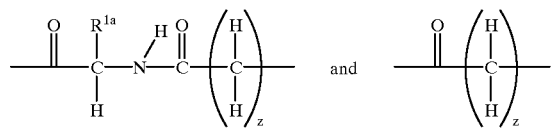

and wherein z is a integer from 0 to 18, or a pharmaceutically acceptable isomer and salt thereof.

13. The compound of claim 10, wherein X is a member selected from the group consisting of:

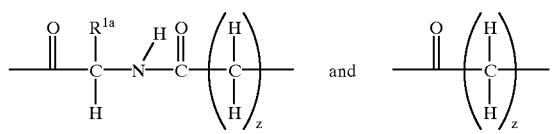

and wherein z is a integer 6–12, or a pharmaceutically acceptable isomer and salt thereof.

14. The compound of claim 10, wherein X is a member selected from the group consisting of:

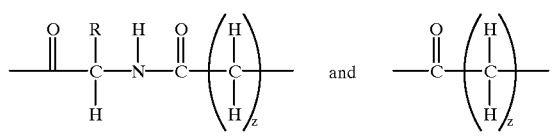

and wherein z is a integer 6–12, or a pharmaceutically acceptable isomer and salt thereof.

15. The compound of claim 2, wherein the Q group is a chitosan compound modified by attaching a sufficient number of organic acyl groups to hydroxyl groups, amino groups or amino and hydroxyl groups, to cause the modified chitosan to absorb or associate both lipids and water and to form a substantially homogenous gel with lipids and water.

16. A method for producing a compound of claim 1, comprising reacting a compound of the formula:

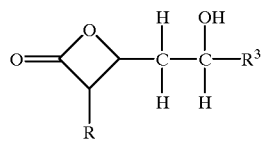

with a compound of the formula

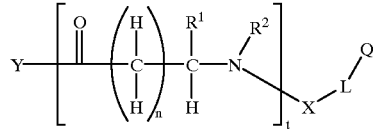

wherein t is 0 or 1 and Y is a leaving group for an etherification or esterification reaction with the hydroxy group to produce a compound of the formula:

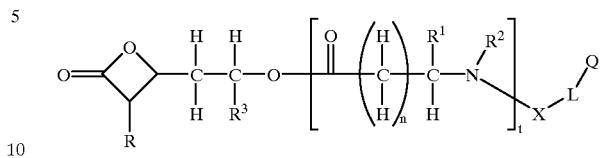

or a salt thereof.

17. A pharmaceutical composition comprising at least one pharmaceutically acceptable carrier excipient and an amount of at least one compound according to claim 1 in a therapeutically effective amount with respect to limiting or preventing the absorption of some dietary fat.

18. A pharmaceutical composition according to claim 17, further comprising a therapeutically effective amount of an oil absorbing effective amount of polysaccharide such as chitosan.

19. A method of using a compound according to claim 1 as a therapeutic agent for disease states in a mammal having at least one disorder that is due to undesired absorption of dietary fat or for reducing the effective caloric intake of a mammal who consumes dietary fat.

20. A method according to claim 18 as part of a treatment method for managing or controlling undesired weight gain or obesity.

21. A method of using a composition according to claim 16 as a therapeutic agent for disease states in a mammal having at least one disorder that is due to undesired absorption of dietary fat or for reducing the effective caloric intake of a mammal who consumes dietary fat.

22. A compound according to claim 2, wherein organic acyl groups are present on the modified chitosan chain of the Q group in a molar ratio from 1 to 8 times the number of the molar ratio of esterified lipase inhibitor alcohol groups.

23. A compound according to claim 2, wherein the hydroxyl groups, amino groups or both hydroxyl and amino groups of Q are modified by the attachment of a sufficient number of organic acyl groups to cause Q to absorb or associate with both lipids and water and to form a substantially homogeneous gel with lipids and water.

* * * * *